(12) United States Patent
Finley et al.

(10) Patent No.: US 12,293,813 B2
(45) Date of Patent: May 6, 2025

(54) HOME AND VEHICLE REPAIR DIAGNOSTICS

(71) Applicant: STATE FARM MUTUAL AUTOMOBILE INSURANCE COMPANY, Bloomington, IL (US)

(72) Inventors: Eric Allyn Finley, Bloomington, IL (US); Jennifer L. Crawford, Normal, IL (US); Corin Rebekah Chapman, Bloomington, IL (US); Edward W Breitweiser, Bloomington, IL (US); Gregory Wong, New Albany, OH (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 135 days.

(21) Appl. No.: 18/099,877

(22) Filed: Jan. 20, 2023

(65) Prior Publication Data

US 2024/0169601 A1    May 23, 2024

Related U.S. Application Data

(60) Provisional application No. 63/428,723, filed on Nov. 29, 2022, provisional application No. 63/427,596, (Continued)

(51) Int. Cl.
*G16H 20/00* (2018.01)
*B60S 5/00* (2006.01)
(Continued)

(52) U.S. Cl.
CPC ............... *G16H 20/00* (2018.01); *B60S 5/00* (2013.01); *G06T 7/20* (2013.01); *G06T 11/00* (2013.01);
(Continued)

(58) Field of Classification Search
CPC .................................................. G06T 19/006
See application file for complete search history.

(56) References Cited

U.S. PATENT DOCUMENTS 9,830,748 B2   11/2017   Rosenbaum
9,990,782 B2   6/2018    Rosenbaum
(Continued)

FOREIGN PATENT DOCUMENTS

EP   3239686 A1   11/2017
EP   3578433 B1   8/2020
(Continued)

*Primary Examiner* — Shivang I Patel
(74) *Attorney, Agent, or Firm* — MARSHALL, GERSTEIN & BORUN LLP

(57) ABSTRACT

Systems and methods for providing augmented reality overlay displays related to repairs may include obtaining sensor data associated with a home or vehicle and analyzing the sensor data associated to identify a vehicle component and/or home appliance that is not functioning properly. Repairs for the vehicle component and/or home appliance that is not functioning properly may be identified, and a determination may be made as to whether it is safe for a vehicle operator and/or home resident to perform the repair. If so, an augmented reality overlay display may be presented upon images/video of the vehicle/home captured in real time, identifying vehicle/home components that must be manipulated in order to perform the repair. If not, the augmented reality display may identify portions of the vehicle or home of which the vehicle operator must capture images in order to request a professional repair or submit an insurance claim.

7 Claims, 8 Drawing Sheets

Related U.S. Application Data filed on Nov. 23, 2022, provisional application No. 63/427,495, filed on Nov. 23, 2022, provisional application No. 63/427,680, filed on Nov. 23, 2022.

(51) Int. Cl.
| | |
|---|---|
| *G06T 7/20* | (2017.01) |
| *G06T 11/00* | (2006.01) |
| *G06V 20/20* | (2022.01) |
| *G07C 5/08* | (2006.01) |
| *G08B 21/04* | (2006.01) |
| *G08B 21/18* | (2006.01) |
| *G08B 21/22* | (2006.01) |
| *G08B 31/00* | (2006.01) |
| *G16H 40/67* | (2018.01) |
| *G16H 50/20* | (2018.01) |

(52) U.S. Cl.
CPC ........... *G06V 20/20* (2022.01); *G07C 5/0808* (2013.01); *G08B 21/0476* (2013.01); *G08B 21/0484* (2013.01); *G08B 21/182* (2013.01); *G08B 21/22* (2013.01); *G08B 31/00* (2013.01); *G16H 40/67* (2018.01); *G16H 50/20* (2018.01); *G06T 2200/24* (2013.01); *G06T 2207/30268* (2013.01)

(56) References Cited

U.S. PATENT DOCUMENTS

| | | | |
|---|---|---|---|
| 10,269,190 B2 | 4/2019 | Rosenbaum | |
| 10,467,824 B2 | 11/2019 | Rosenbaum | |
| 11,227,452 B2 | 1/2022 | Rosenbaum | |
| 11,407,410 B2 | 8/2022 | Rosenbaum | |
| 11,524,707 B2 | 12/2022 | Rosenbaum | |
| 11,532,051 B1 * | 12/2022 | Braun | G06Q 40/08 |
| 11,594,083 B1 | 2/2023 | Rosenbaum | |
| 2019/0278992 A1 * | 9/2019 | Hossain | G06Q 10/20 |
| 2020/0357204 A1 * | 11/2020 | Crequer | G07C 5/0841 |
| 2022/0092557 A1 * | 3/2022 | Antony | G06F 3/011 |
| 2022/0092893 A1 | 3/2022 | Rosenbaum | |
| 2022/0340148 A1 | 10/2022 | Rosenbaum | |
| 2023/0060300 A1 | 3/2023 | Rosenbaum | |

FOREIGN PATENT DOCUMENTS

| | | | |
|---|---|---|---|
| EP | 3730375 | B1 | 10/2021 |
| EP | 3960576 | A1 | 3/2022 |
| EP | 4190659 | A1 | 6/2023 |
| EP | 4190660 | A1 | 6/2023 |

* cited by examiner

HOME AND VEHICLE REPAIR DIAGNOSTICS

CROSS-REFERENCE TO RELATED APPLICATIONS

The present application claims priority to U.S. Provisional Patent Application No. 63/427,596, entitled "Homeowner Health Alerts and Mitigation based on Home Sensor Data," and filed Nov. 23, 2022; U.S. Provisional Patent Application No. 63/428,723, entitled "Homeowner Health Alerts and Mitigation based on Home Sensor Data," and filed Nov. 29, 2022;" U.S. Provisional Patent Application No. 63/427,495, entitled "Home Condition Alerts based on Home Sensor Data," and filed Nov. 23, 2022; and U.S. Provisional Patent Application No. 63/427,680, entitled "Home and Vehicle Repair Diagnostics," and filed Nov. 23, 2022; the disclosures of each of which are incorporated by reference herein.

FIELD OF THE INVENTION

The present disclosure generally relates to technologies associated with home and vehicle repairs, more particularly, to technologies for providing augmented reality overlay displays related to repairs.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

When a home appliance or a vehicle component is not functioning properly, it may sometimes be difficult for users (e.g., residents of the home, vehicle operators, etc.) to identify that something is wrong. In particular, users may not realize there is an issue until the home appliance or the vehicle component has deteriorated severely, which may lead to health and/or safety concerns in some cases. Even if a user realizes that the home appliance or vehicle component is not functioning properly, determining what type of repair is needed, what the steps or stages of that repair might be, and/or whether it is safe (or possible) for the user to perform the repair without the assistance of a professional may be overwhelming for the user. Conventional techniques may include additional inefficiencies, encumbrances, ineffectiveness, and/or other drawbacks.

SUMMARY

The present embodiments may relate to, inter alia, technologies associated with home and vehicle repairs, as well as technologies for providing augmented (or other semi-virtual, quasi-virtual, or virtual) reality overlay displays related to home and/or vehicle repairs.

In one aspect, a computer-implemented method for providing augmented reality overlay displays related to vehicle repairs may be provided. The method may be implemented via one or more local or remote processors, transceivers, sensors, servers, vehicles, vehicle-mounted processors and sensors, mobile devices, wearables, smart contact lenses, virtual headsets (e.g., virtual reality headsets, smart glasses, augmented reality glasses, mixed or extended reality glasses or headsets, etc.), and/or other electronic or electric components, which may be in wired or wireless communication with one another and/or other devices. In one instance, the method may include (1) obtaining, by one or more processors, sensor data associated with the vehicle captured by one or more permanent or temporary in-vehicle sensors; (2) analyzing, by the one or more processors, the sensor data associated with the vehicle in order to identify a vehicle component that is not functioning properly; (3) identifying, by the one or more processors, at least one possible repair for the vehicle component that is not functioning properly; (4) determining, by the one or more processors, whether it is safe for a vehicle operator to perform the at least one repair for the vehicle component that is not functioning properly; (5) based upon determining that it is safe for the vehicle operator to perform the at least one repair for the vehicle component that is not functioning properly: presenting an augmented reality (or other virtual reality or semi-virtual reality) overlay display upon images or video of the vehicle captured in real time, wherein the augmented reality overlay display identifies vehicle components that must be manipulated in order to perform the at least one repair; and/or (6) based upon determining that it is not safe for the vehicle operator to perform the at least one repair for the vehicle component that is not functioning properly: presenting an augmented reality overlay display upon images or video of the vehicle captured in real time, wherein the augmented reality overlay display identifies portions of the vehicle of which the vehicle operator must capture images in order to one or more of: (i) request a professional repair of the vehicle component or (ii) prepare and/or submit an insurance claim (such as a virtual or electronic insurance claim) related to the vehicle component that is not functioning properly. The method may include additional, less, or alternate actions, including those discussed elsewhere herein.

In another aspect, a computer system for providing augmented reality overlay displays related to vehicle repairs may be provided. The computer system may include one or more local or remote processors, transceivers, sensors, servers, vehicles, vehicle-mounted processors and sensors, mobile devices, wearables, smart contacts, virtual headsets (e.g., virtual reality headsets, smart glasses, augmented reality glasses, mixed or extended reality headsets or glasses, etc.), and/or other electronic or electric components. In one instance, the computer system may include one or more processors and a memory storing computer-executable instructions that, when executed by the one or more processors, cause the one or more processors to: (1) obtain sensor data associated with the vehicle captured by one or more permanent or temporary in-vehicle sensors; (2) analyze the sensor data associated with the vehicle in order to identify a vehicle component that is not functioning properly; (3) identify at least one possible repair for the vehicle component that is not functioning properly; (4) determine whether it is safe for a vehicle operator to perform the at least one repair for the vehicle component that is not functioning properly; (5) based upon determining that it is safe for the vehicle operator to perform the at least one repair for the vehicle component that is not functioning properly: present an augmented reality (or other virtual reality or semi-virtual reality) overlay display upon images or video of the vehicle captured in real time, wherein the augmented reality (or other virtual reality or semi-virtual reality) overlay display identifies vehicle components that must be manipulated in order to perform the at least one repair; and/or (6) based upon determining that it is not safe for the vehicle operator to perform the at least one repair for the vehicle component that is not functioning properly: present an augmented reality overlay display upon images or video of the vehicle captured in real time, wherein the augmented reality overlay display identifies portions of the vehicle of which the vehicle operator must capture images in order to one or more of: (i) request a professional repair of the vehicle component, or (ii) prepare and/or submit an insurance claim (such as a virtual or electronic insurance claim) related to the vehicle component that is not functioning properly. The system may include additional, less, or alternate functionality, including that discussed elsewhere herein.

In still another aspect, a non-transitory computer-readable storage medium storing computer-readable instructions for providing augmented reality overlay displays related to vehicle repairs may be provided. The computer-readable instructions, when executed by one or more processors, cause the one or more processors to: (1) obtain sensor data associated with the vehicle captured by one or more permanent or temporary in-vehicle sensors; (2) analyze the sensor data associated with the vehicle in order to identify a vehicle component that is not functioning properly; (3) identify at least one possible repair for the vehicle component that is not functioning properly; (4) determine whether it is safe for a vehicle operator to perform the at least one repair for the vehicle component that is not functioning properly; (5) based upon determining that it is safe for the vehicle operator to perform the at least one repair for the vehicle component that is not functioning properly: present an augmented reality (or other virtual reality or semi-virtual reality) overlay display upon images or video of the vehicle captured in real time, wherein the augmented reality overlay display identifies vehicle components that must be manipulated in order to perform the at least one repair; and/or (6) based upon determining that it is not safe for the vehicle operator to perform the at least one repair for the vehicle component that is not functioning properly: present an augmented reality overlay display upon images or video of the vehicle captured in real time, wherein the augmented reality overlay display identifies portions of the vehicle of which the vehicle operator must capture images in order to one or more of: (i) request a professional repair of the vehicle component or (ii) prepare and/or submit an insurance claim (such as a virtual or electronic insurance claim) related to the vehicle component that is not functioning properly. The instructions may direct additional, less, or alternative functionality, including that discussed elsewhere herein.

In another aspect, a computer-implemented method for providing augmented reality overlay displays related to home repairs may be provided. The method may be implemented via one or more local or remote processors, transceivers, sensors, servers, vehicles, mobile devices, wearables, smart contacts, virtual headsets (e.g., virtual reality headsets, smart glasses, augmented reality glasses, mixed or extended reality headsets or glasses, etc.), and/or other electronic or electric components, which may be in wired or wireless communication with one another and/or other devices. In one instance, the method may include (1) obtaining, by one or more processors, sensor data associated with the home environment captured by one or more in-home sensors; (2) analyzing, by the one or more processors, the sensor data associated with the home environment in order to identify a home appliance that is not functioning properly; (3) identifying, by the one or more processors, at least one possible repair for the home appliance that is not functioning properly; (4) determining, by the one or more processors, whether it is safe for a resident of the home to perform the at least one repair for the home appliance that is not functioning properly; (5) based upon determining that it is safe for the resident of the home to perform the at least one repair for the home appliance that is not functioning properly: presenting an augmented reality (or other virtual reality or semi-virtual reality) overlay display upon images or video of the home environment in real time, wherein the augmented reality overlay display identifies home components that must be manipulated in order to perform the at least one repair; and/or (6) based upon determining that it is not safe for the resident of the home to perform the at least one repair for the home appliance that is not functioning properly: presenting an augmented reality (or other virtual reality or semi-virtual reality) overlay display upon images or video of the vehicle in real time, wherein the augmented reality overlay display identifies areas of the home environment of which the resident of the home must capture images in order to one or more of: (i) request a professional repair for the home appliance or (ii) prepare and/or submit an insurance claim (such as a virtual or electronic insurance claim) related to the home appliance that is not functioning properly. The method may include additional, less, or alternate actions, including those discussed elsewhere herein.

In still another aspect, a computer system for providing augmented reality overlay displays related to home repairs may be provided. The computer system may include one or more local or remote processors, transceivers, sensors, servers, mobile devices, wearables, smart contact lenses, virtual headsets (e.g., virtual reality headsets, smart glasses, augmented reality glasses, mixed or extended reality headsets or glasses, etc.), and/or other electronic or electric components. In one instance, the computer system may include one or more processors and a memory storing computer-executable instructions that, when executed by the one or more processors, cause the one or more processors to: (1) obtain sensor data associated with a home environment captured by one or more in-home sensors; (2) analyze the sensor data associated with the home environment in order to identify a home appliance that is not functioning properly; (3) identify at least one possible repair for the home appliance that is not functioning properly; (4) determine whether it is safe for a resident of the home to perform the at least one repair for the home appliance that is not functioning properly; (5) based upon determining that it is safe for the resident of the home to perform the at least one repair for the home appliance that is not functioning properly: present an augmented reality (or other virtual reality or semi-virtual reality) overlay display upon images or video of the home environment in real time, wherein the augmented reality overlay display identifies home components that must be manipulated in order to perform the at least one repair; and/or (6) based upon determining that it is not safe for the resident of the home to perform the at least one repair for the home appliance that is not functioning properly: present an augmented reality (or other virtual reality or semi-virtual reality) overlay display upon images or video of the vehicle in real time, wherein the augmented reality overlay display identifies areas of the home environment of which the resident of the home must capture images in order to one or more of: (i) request a professional repair for the home appliance or (ii) prepare and/or submit an insurance claim (such as a virtual or electronic insurance claim) related to the home appliance that is not functioning properly. The system may include additional, less, or alternate functionality, including that discussed elsewhere herein.

In another aspect, a non-transitory computer-readable storage medium storing computer-readable instructions for providing augmented reality overlay displays related to home repairs is provided. The computer-readable instructions, when executed by one or more processors, cause the one or more processors to: (1) obtain sensor data associated with a home environment captured by one or more in-home sensors; (2) analyze the sensor data associated with the home environment in order to identify a home appliance that is not functioning properly; (3) identify at least one possible repair for the home appliance that is not functioning properly; (4) determine whether it is safe for a resident of the home to perform the at least one repair for the home appliance that is not functioning properly; (5) based upon determining that it is safe for the resident of the home to perform the at least one repair for the home appliance that is not functioning properly: present an augmented reality (or other virtual reality or semi-virtual reality) overlay display upon images or video of the home environment in real time, wherein the augmented reality overlay display identifies home components that must be manipulated in order to perform the at least one repair; and/or (6) based upon determining that it is not safe for the resident of the home to perform the at least one repair for the home appliance that is not functioning properly: present an augmented reality overlay (or other virtual reality or semi-virtual reality) display upon images or video of the vehicle in real time, wherein the augmented reality overlay display identifies areas of the home environment of which the resident of the home must capture images in order to one or more of: (i) request a professional repair for the home appliance, or (ii) prepare and/or submit an insurance claim (such as a virtual or electronic insurance claim) related to the home appliance that is not functioning properly. The instructions may direct additional, less, or alternative functionality, including that discussed elsewhere herein.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof.

There are shown in the drawings arrangements which are presently discussed, it being understood, however, that the present embodiments are not limited to the precise arrangements and instrumentalities shown, wherein.

Figure 1:
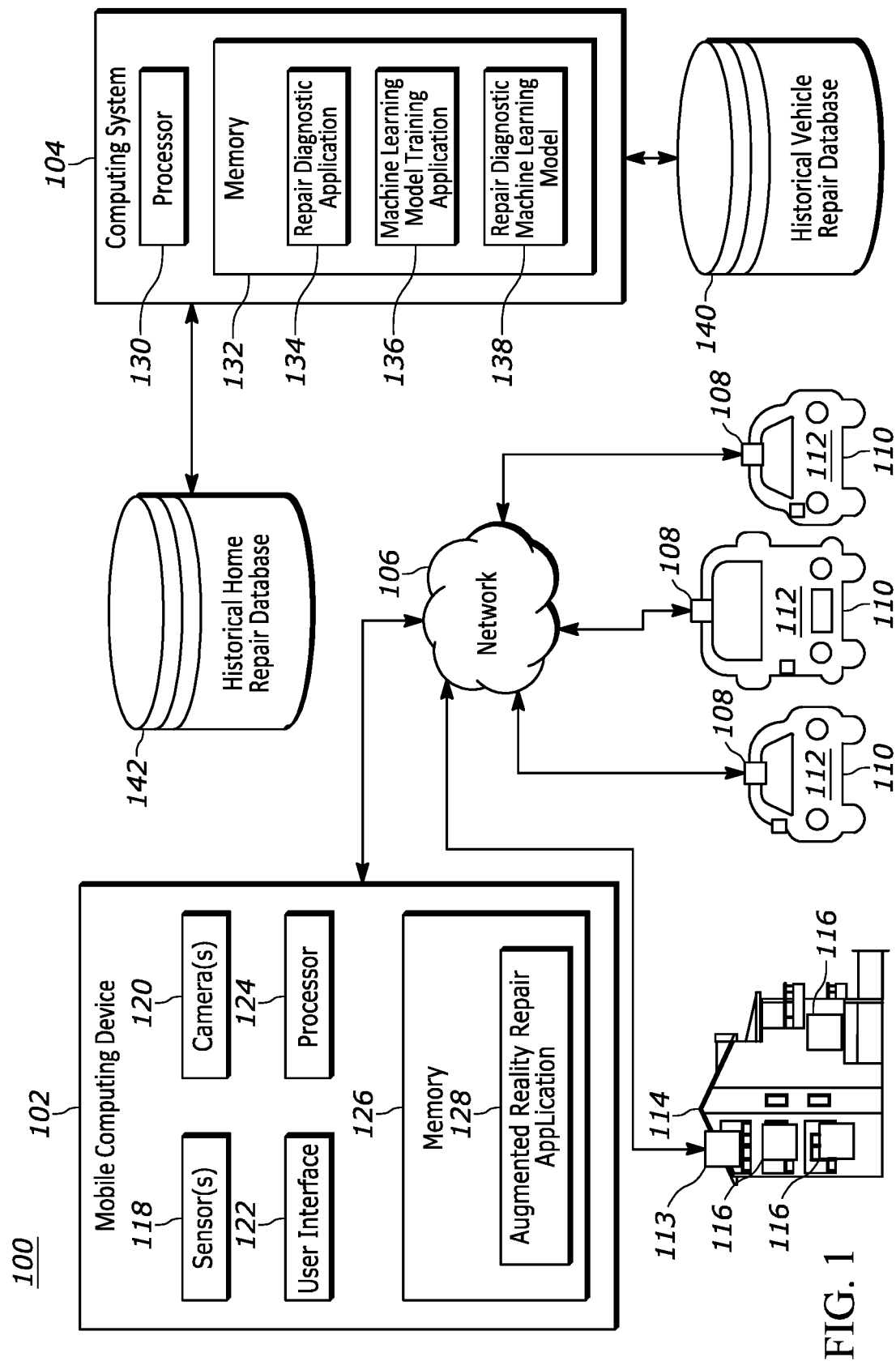
FIG. 1 depicts an exemplary computer system for providing augmented reality overlay displays related to repairs, according to one embodiment.

While the systems and methods disclosed herein is susceptible of being embodied in many different forms, it is shown in the drawings and will be described herein in detail specific exemplary embodiments thereof, with the understanding that the present disclosure is to be considered as an exemplification of the principles of the systems and methods disclosed herein and is not intended to limit the systems and methods disclosed herein to the specific embodiments illustrated. In this respect, before explaining at least one embodiment consistent with the present systems and methods disclosed herein in detail, it is to be understood that the systems and methods disclosed herein is not limited in its application to the details of construction and to the arrangements of components set forth above and below, illustrated in the drawings, or as described in the examples.

Methods and apparatuses consistent with the systems and methods disclosed herein are capable of other embodiments and of being practiced and carried out in various ways. Also, it is to be understood that the phraseology and terminology employed herein, as well as the abstract included below, are for the purposes of description and should not be regarded as limiting.

DETAILED DESCRIPTION

Using the techniques provided herein, data captured by vehicle and/or home sensors may be used to, inter alia, identify and/or diagnose components of a vehicle and/or home that are not functioning properly, and to identify possible repairs that may be needed. For instance, vehicle issues in need of repair may be diagnosed based upon analyzing vehicle sensor data (in some cases, combined with vehicle operational data) captured over a period of time, e.g., using a machine learning model trained based upon historical sensor and/or operational data associated with various vehicles and historical vehicle issues and repairs associated therewith. Similarly, home issues in need of repair may be diagnosed based upon analyzing home sensor data (in some cases, combined with home operational data) captured over a period of time, e.g., using a machine learning model trained based upon historical sensor and/or operational data associated with various homes and historical home issues and repairs associated therewith.

For an identified vehicle or home issue in need of repair, the techniques provided herein may provide a prediction and/or identification of the issue and a prediction and/or identification of possible repairs for the issue. Furthermore, the application may provide an indication of whether the issue may be easily and/or safely repaired by the vehicle operator or home resident themselves, or whether it would be best for a professional to perform the repair. If the issue may be easily and/or safely repaired by the vehicle operator or home resident themselves, an augmented reality (AR) overlay display may be presented over real-time images or video of the vehicle or home that are captured by the user, identifying vehicle or home components that must be physically manipulated in order to complete one or more identified steps of the repair. Additionally or alternatively, one or more virtual reality (VR), semi-reality, or quasi-reality overlay displays may be generated or displayed, such as on smart glasses, smart contacts, augmented reality glasses, virtual reality headsets or glasses, mixed or extended reality glasses or headsets, etc.

If the repair should be performed by a professional, the application may provide a price estimate for the repair and/or a listing of professionals in the area who are capable of performing the repair. Moreover, the application may provide an indication of whether an existing insurance policy covers the issue, and if so, an indication of photos or videos of the issue that may be taken by the user for a streamlined claim submission. For instance, an AR overlay display may be presented over real-time images or video of the vehicle or home that are captured by the user, identifying vehicle or home components of which images or videos should be captured, as well as angles, zoom levels, or other specifications for how the images or videos should be captured.

Exemplary System for Providing Augmented Reality Overlay Displays Related to Repairs Referring now to the drawings, FIG. 1 depicts an exemplary computer system 100 for providing augmented reality overlay displays (or other virtual reality or semi-virtual reality overlays and/or displays) related to repairs, according to one embodiment. The high-level architecture illustrated in FIG. 1 may include both hardware and software applications, as well as various data communications channels for communicating data between the various hardware and software components, as is described below.

The system 100 may include a mobile computing device 102 (which may include, e.g., a smart phone, a smart watch or fitness tracker device, a tablet, a laptop, a virtual reality headset, smart or augmented reality glasses, smart glasses, mixed or extended reality glasses or headsets, wearables, etc.), a computing system 104 (which is described in greater detail below with respect to FIG. 6) one or more vehicle computing devices 108, associated with respective vehicles 110 and vehicle sensors 108, and/or one or more home computing device 113 associated with respective homes 114 and home sensors 116. The vehicles 110 may be autonomous vehicles, semi-autonomous vehicles, or connected manual vehicles, in various embodiments. In certain examples, in which the vehicles 110 are autonomous or semi-autonomous vehicles, the vehicle computing devices 108 may at least partially control the operation of the vehicles. The mobile computing device 102, computing system 104, the vehicle computing devices 108, and/or the home computing devices 113 may be configured to communicate with one another via a wired or wireless computer network 106.

Each of the vehicle computing devices 108 may include, or may be configured to communicate with, one or more respective sensors 112 associated with respective vehicles 110. For instance, the sensors 112 may include onboard interior (e.g., including the interior of the cabin of the vehicle and/or the interior of the hood and/or trunk of the vehicle) or exterior sensors. The sensors 112 may be configured to capture interior and/or exterior sensor data associated with respective vehicles 110, including image or video data (e.g., captured by one or more cameras), motion data (e.g., captured by one or more motion detectors), audio data (e.g., captured by one or more microphones), location data (e.g., captured by one or more global positioning systems [GPS] and/or other locationing systems), movement data (e.g., captured by one or more accelerometers and/or gyroscopes), temperature data (e.g., captured by one or more temperature sensors), humidity data (e.g., captured by one or more humidity sensors), air flow data (e.g., captured by one or more air flow sensors), etc.

Moreover, the sensors 112 may include sensors integrated within or positioned on various vehicle components, including but not limited to the engine, the transmission system, the battery, the alternator, the fuel system, the radiator, the axles, the suspension system, the braking system, the catalytic converter, the muffler, the tailpipe, the fuel tank, the tires, the seats, the air conditioning unit, the stereo and/or radio, the windshield wiper, the gear shift, the steering wheel, the doors, the windows and/or window controls, the sunroof, the ammeter, the clinometer, the dynamometer, the fuel gauge, the manometer, the hydrometer, the odometer (also called milometer or mileometers), the speedometer, the tachometer, the temperature gauge, the tire pressure gauge, the vacuum gauge, the voltmeter, the water temperature meter, the oil pressure gauge, the ignition system, the lighting system, the alarm, the horn, the air bag control, the fuse box, the lock system, etc.

Moreover, each of the vehicle computing devices 108 may be configured to collect (or may communicate with other devices configured to collect) vehicle operational data. For instance, the vehicle operational data may include indications of vehicle controls and/or operations performed by a vehicle operator, usage data, and/or settings adjusted by the vehicle operator for various vehicle components, as well as dates and/or times associated with controls, operations, usage, and/or settings. For instance, the operational data may include data associated with turning operations, steering operations, and/or braking operations, as well as air conditioning or heating operations, stereo or radio operations, turn signal operations, windshield wiper operators, headlight (or other lighting) operations, operations involving adjustment of vehicle seating, operations involving adjustment of vehicle mirrors, or controls, operations, usage, and/or settings adjustments of any of the vehicle components discussed above (or any other vehicle components).

Similarly, the home computing devices 113 may include, or may be configured to communicate with, one or more respective sensors 116 associated with a home environment 114. For instance, the sensors 116 may include interior sensors (e.g., including sensors positioned in various rooms of the home) or exterior sensors (e.g., including sensors positioned inside of the home and/or positioned at an exterior wall of the home and configured to capture data associated with a yard, balcony, deck, or patio of the home, and/or sensors positioned external to the home). The sensors 112 may be configured to capture interior and/or exterior sensor data associated with the home environment 114 and/or appliances or components thereof, including image or video data (e.g., captured by one or more cameras), motion data (e.g., captured by one or more motion detectors), audio data (e.g., captured by one or more microphones), movement data (e.g., captured by one or more accelerometers and/or gyroscopes), temperature data (e.g., captured by one or more temperature sensors), humidity data (e.g., captured by one or more humidity sensors), air flow data (e.g., captured by one or more air flow sensors), etc. Furthermore, the sensors 116 may include sensors integrated within or positioned on various home components, home appliances, plumbing fixtures, etc., including but not limited to freezers, refrigerators, water coolers, ice makers, kitchen stoves, ovens, microwave ovens, washing machines, dryers, dishwashers, air conditioners, heaters, furnaces, water heaters, ventilators, toilets, showers, sinks, sump pumps, pool heating and/or filtration equipment, etc.

Moreover, each of the home computing devices 113 may be configured to collect (or may communicate with other devices configured to collect) home operational data. For instance, the home operational data may include indications of home controls and/or operations performed by a resident of the home, usage data, and/or settings adjusted by a home resident for various home components, home appliances, plumbing fixtures, etc., as well as dates and/or times associated with such controls, operations, usage, and/or settings. For instance, the home operational data may include data associated with air conditioning operations or adjustment of settings associated therewith, heating operations or adjustment of settings associated therewith, water heating operations or adjustment of settings associated therewith, cooking operations or adjustment of settings associated therewith, plumbing operations or adjustment of settings associated therewith, dish washing operations or adjustment of settings associated therewith, laundry operations or adjustment of settings associated therewith, pool heating and/or filtration operations or adjustment of settings associated therewith, or any other controls, operations, usage, and/or settings adjustments of any of the home appliances, home components, and/or plumbing fixtures discussed above (or any other home appliances, home components, plumbing fixtures, etc.).

The mobile computing device 102 may include one or more sensors 118, one or more cameras 120, a user interface 122 configured to receive input from users and provide interactive displays to users, and one or more processor(s) 124, as well as one or more computer memories 126. In some examples, the one or more sensors 118 and/or the one or more cameras 120 may include any of the sensors described as vehicle sensors 112 and/or home sensors 116. Moreover, in some examples, data captured by the one or more sensors and/or the one or more cameras 120 may be used in addition to or as an alternative to any of data described as being captured by the vehicle sensors 112 and/or home sensors 116 above.

Memories 126 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. Memorie(s) 126 may store an operating system (OS) (e.g., iOS, Microsoft Windows, Linux, UNIX, etc.) capable of facilitating the functionalities, apps, methods, or other software as discussed herein. Memorie(s) 126 may also store an augmented reality repair application 128.

Executing the augmented reality repair application 128 may include receiving and/or otherwise obtaining the sensor data captured by the vehicle sensors 112, home sensors 116, mobile device sensors 118, and/or mobile device cameras 120, and analyzing the sensor data, and/or vehicle operational data or home operational data, to identify a vehicle component or home appliance (including home components, home fixtures, plumbing fixtures, etc., as discussed above) that is not functioning properly. In some examples, analyzing the sensor data (and/or operational data) to identify the vehicle component or home appliance that is not functioning properly may include applying a trained machine learning model to the sensor data (and/or operational data) to identify or predict the vehicle component or home appliance that is not functioning properly, e.g., by sending the sensor data (and/or operational data) to the computing system 104, on which a trained machine learning model 138 may be executing (described in greater detail below), and by receiving an identification or prediction of the vehicle component or home appliance that is not functioning properly from the computing system 104.

Furthermore, executing the augmented reality repair application 128 may include identifying one or more possible repairs for the vehicle component or home appliance that is not functioning properly. In some examples, identifying the one or more possible repairs for the vehicle component or home appliance that is not functioning properly may include may include applying a trained machine learning model to the sensor data (and/or operational data) and the identified vehicle component or home appliance to identify or predict one or more possible repairs to fix the vehicle component or home appliance that is not functioning properly, e.g., by sending the sensor data (and/or operational data) and an indication of the identified vehicle component or home appliance to the computing system 104, on which a trained machine learning model 138 may be executing (described in greater detail below), and by receiving, from the computing system 104, an identification or prediction of one or more possible repairs to fix the vehicle component or home appliance that is not functioning properly. In some examples, the identification or prediction of the one or more possible repairs may include an identification of one or more steps or stages for the one or more possible repairs.

Moreover, executing the augmented reality repair application 128 may include determining whether the one or more possible repairs (and/or each of the steps of the one or more possible repairs) are safe for an amateur (i.e., non-professional) vehicle operator or home resident to perform themselves, or whether it would be best for a professional to perform the one or more possible repairs. For instance, the augmented reality repair application 128 may analyze each of the steps or stages of the repair to determine any potential health or safety risks associated with each step or stage of the repair. The augmented reality repair application 128 may assign a health or safety risk score to each of potential health or safety risks, and may determine whether it is safe for the vehicle operator and/or home resident to perform the repair by comparing the health or safety risk score of the repair collectively, and/or of each of the individual steps or stages of the repair, to a threshold health or safety risk score.

Additionally, executing the augmented reality repair application 128 may include, based upon determining that it is safe for the vehicle operator and/or home resident to perform the repair themselves, providing an augmented reality display overlay identifying vehicle components or home components that must be manipulated in order to perform the repair. In some examples, e.g., when the mobile device 102 does not include any glasses or windows, the augmented reality repair application 128 may provide the augmented reality display overlay via the user interface 122, overlaid upon images and or videos captured by the camera 120 in real time. In other examples, e.g., when the mobile device 102 include smart glasses or augmented reality glasses, or otherwise includes windows, the augmented reality repair application 128 may provide the augmented reality display overlay via the user interface 122, overlaid upon glasses or windows of the mobile device 102.

Figure 2A:
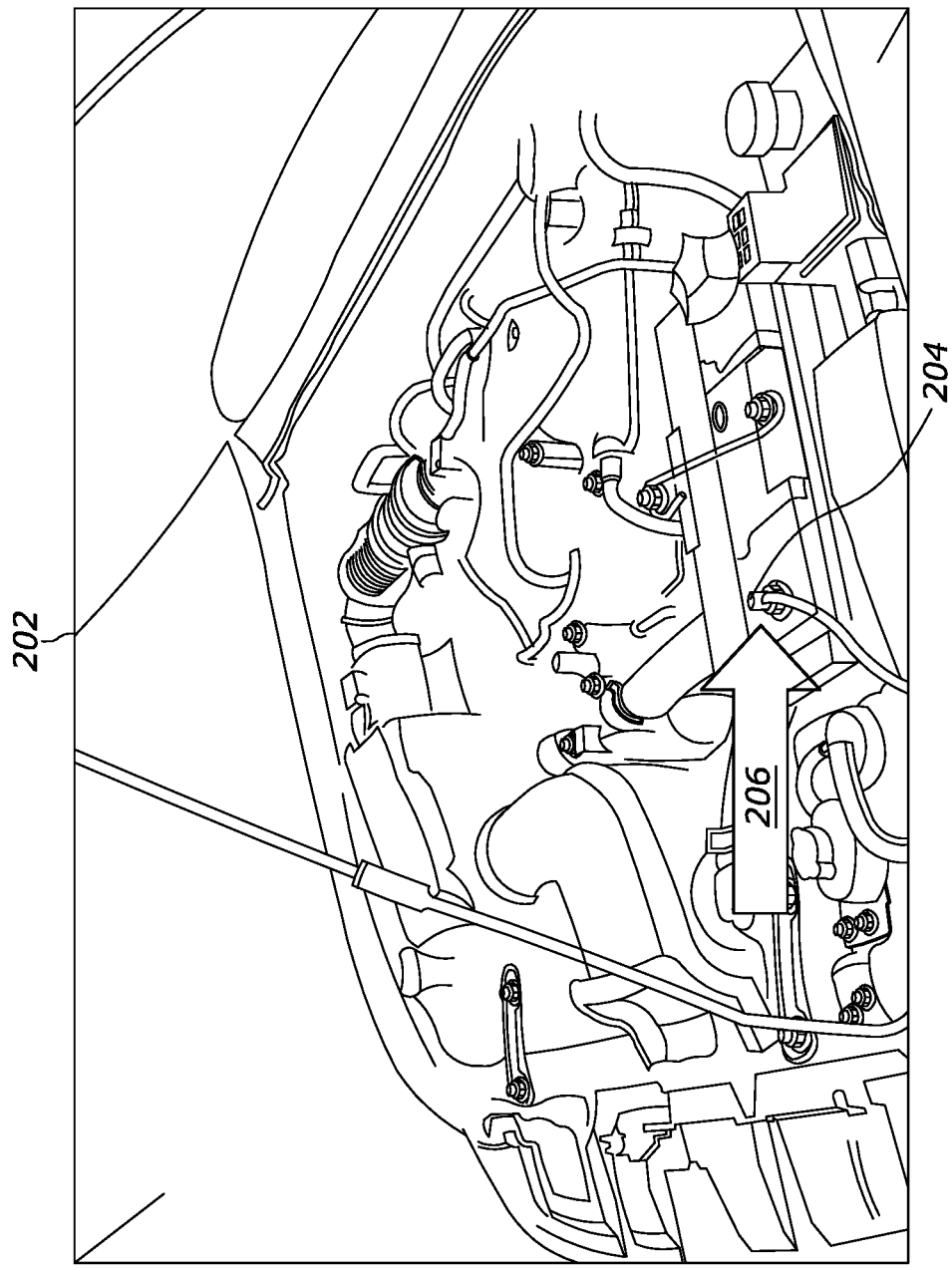
FIG. 2A depicts an exemplary augmented reality display identifying vehicle components that must be manipulated in order to perform a repair, according to one embodiment.

An example of the augmented reality display overlay in the case of the vehicle repair is shown at FIG. 2A. As shown at FIG. 2A, a view 202 of a portion of the vehicle (i.e., either images or videos captured by the camera 120 in real time, or a view through glasses or a window) may include at least one vehicle component 204 that must be manipulated in order to perform the repair. An augmented reality display overlay 206 may identify or otherwise indicate the vehicle component 204 that must be manipulated in order to perform the repair.

In examples in which the repair includes multiple steps or stages, the augmented reality repair application 128 may provide an augmented reality display overlay 206 identifying a first vehicle component 204 that must be manipulated in order to perform the first stage or step of the repair. The augmented reality repair application 128 may also provide an indication of how the vehicle component 204 must be manipulated in order to perform the first stage or step of the repair. The augmented reality repair application 128 may then determine whether the first stage or step of the repair is complete, e.g., by analyzing the images or videos captured by the camera 120 of the operator of the vehicle performing the repair, or of the vehicle component 204 after manipulation, or by receiving an indication from the user, e.g., via the user interface 122, indicating that the first stage or step of the repair is complete.

Upon determining that the first stage or step of the repair is complete, the augmented reality repair application 128 may provide an augmented reality display overlay 206 for a second stage or step of the repair (e.g., indicating a different vehicle component 204 to be manipulated, or indicating a different way in which the original vehicle component 204 must be manipulated) in a similar manner. Subsequently, upon determining that the second stage or step of the repair is complete, the augmented reality application 128 may provide an augmented reality display overlay 206 for a third stage or step of the repair, and so on until all stages or steps of the repair are complete.

Figure 3A:
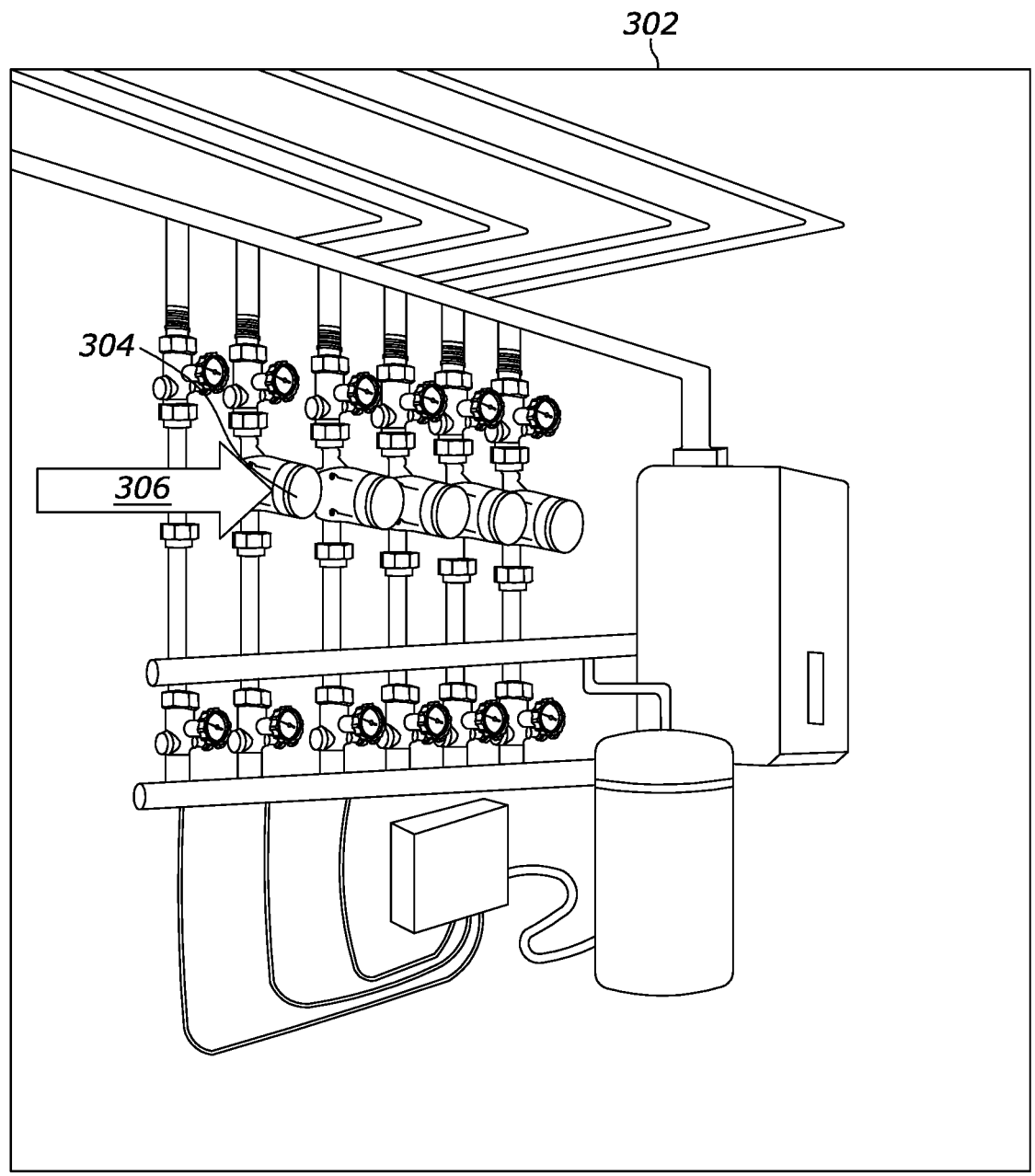
FIG. 3A depicts an exemplary augmented reality display identifying home components that must be manipulated in order to perform a repair, according to one embodiment.

Similarly, an example of the augmented reality display overlay in the case of the home repair is shown at FIG. 3A. As shown at FIG. 3A, a view 302 of a portion of the vehicle (i.e., either images or videos captured by the camera 120 in real time, or a view through glasses or a window) may include at least one home component 304 that must be manipulated in order to perform the repair. An augmented reality display overlay 306 may identify or otherwise indicate the home component 304 that must be manipulated in order to perform the repair.

In examples in which the repair includes multiple steps or stages, the augmented reality repair application 128 may provide an augmented reality display overlay 306 identifying a first home component 304 that must be manipulated in order to perform the first stage or step of the repair. The augmented reality repair application 128 may also provide an indication of how the home component 304 must be manipulated in order to perform the first stage or step of the repair. The augmented reality repair application 128 may then determine whether the first stage or step of the repair is complete, e.g., by analyzing the images or videos captured by the camera 120 of the resident of the home performing the repair, or of the home component 304 after manipulation, or by receiving an indication from the user, e.g., via the user interface 122, indicating that the first stage or step of the repair is complete.

Upon determining that the first stage or step of the repair is complete, the augmented reality repair application 128 may provide an augmented reality display overlay 306 for a second stage or step of the repair (e.g., indicating a different home component 304 to be manipulated, or indicating a different way in which the original home component 304 must be manipulated) in a similar manner. Subsequently, upon determining that the second stage or step of the repair is complete, the augmented reality application 128 may provide an augmented reality display overlay 306 for a third stage or step of the repair, and so on until all stages or steps of the repair are complete.

Additionally, executing the augmented reality repair application 128 may include, based upon determining that it is not safe for the vehicle operator and/or home resident to perform the repair themselves, providing an estimated cost for a professional repair, as well as an indication of whether an existing insurance policy covers the issue. Furthermore, executing the augmented reality repair application 128 may include providing augmented reality display overlay identifying portions or areas of the vehicle or the home of which images or videos must be captured in order to request the professional repair, and/or in order to prepare and/or submit an insurance claim for the repair. In some examples, the augmented reality repair application 128 may provide, for instance, indications of angles, zoom levels, etc., or other specifications for how the images or videos should be captured.

Additionally or alternatively, the augmented reality repair application may present a virtual or electronic insurance claim (such as one prepared by one or more local or remote processors or servers) for the insured's or other user's review, modification, or approval. For instance, after the images or videos are captured by user's device, the image or video data may be transmitted to one or more local or remote processors and/or servers for analysis. The local or remote processors or servers may generate a virtual insurance claim with pre-populated fields, and transmit the virtual insurance claim to the insured's or other user's mobile device, wearable, virtual or augmented reality headset or glasses, etc. for their review, modification, approval, and/or submission.

As discussed above, in some examples, e.g., when the mobile device 102 does not include any glasses or windows, the augmented reality repair application 128 may provide the augmented reality display overlay via the user interface 122, overlaid upon images and or videos captured by the camera 120 in real time. In other examples, e.g., when the mobile device 102 include smart glasses or augmented reality glasses, or otherwise includes windows, the augmented reality repair application 128 may provide the augmented reality display overlay via the user interface 122, overlaid upon glasses or windows of the mobile device 102.

Figure 2B:
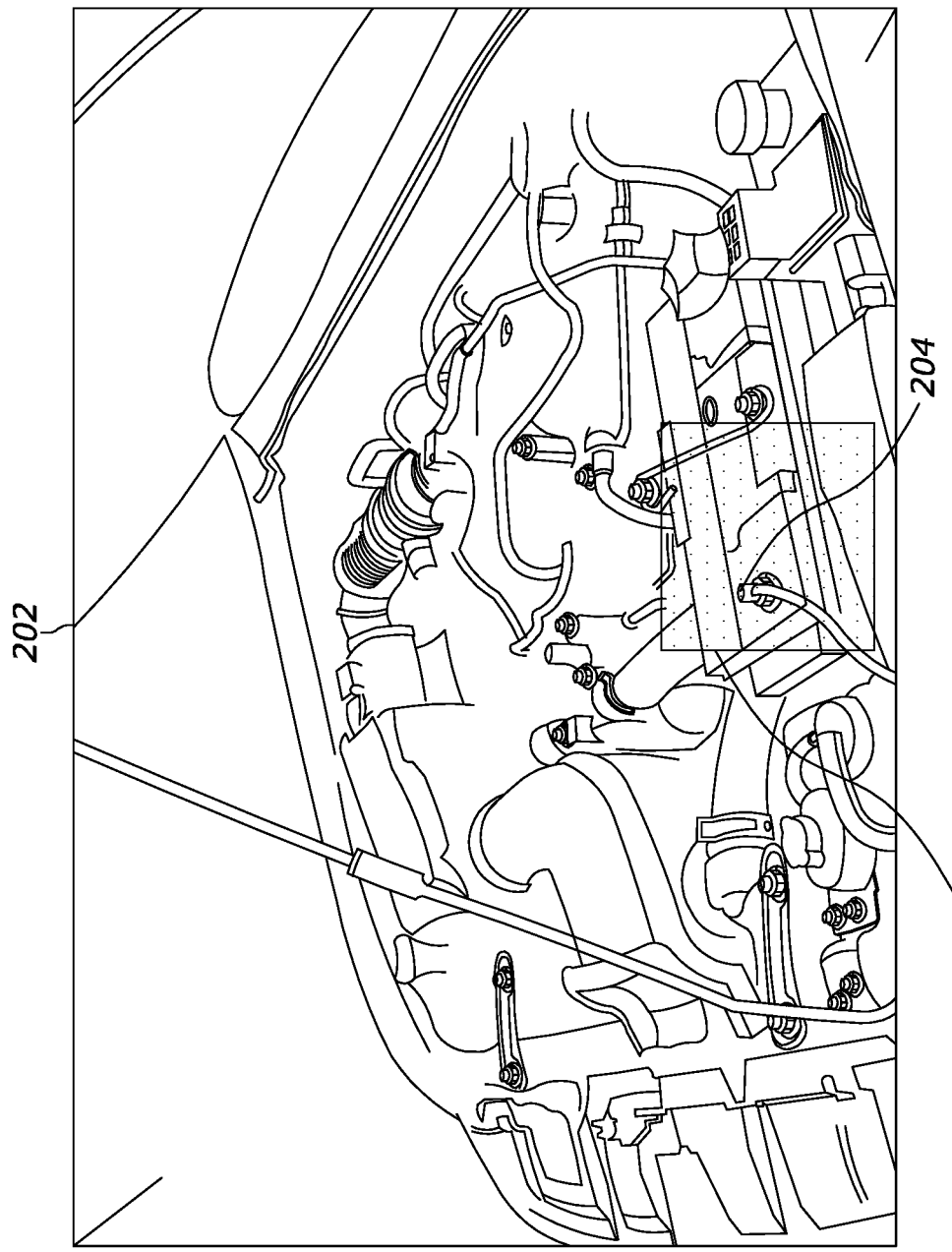
FIG. 2B depicts an exemplary augmented reality display identifying portions of a vehicle of which images may be captured in order to request a professional repair of a vehicle component that is not functioning properly, and/or submit an insurance claim related to the vehicle component that is not functioning properly, according to one embodiment.

An example of the augmented reality display overlay in the case of the vehicle repair is shown at FIG. 2B. As shown at FIG. 2B, a view 202 of a portion of the vehicle (i.e., either images or videos captured by the camera 120 in real time, or a view through glasses or a window) may include at least one augmented reality display overlay 208 identifying or otherwise indicating a portion or area of the vehicle of which an image or video must be captured. In examples in which multiple images or videos must be captured, the augmented reality repair application 128 may provide a first augmented reality display overlay 208 identifying a first portion or area of the vehicle of which an image or video must be captured. The augmented reality repair application 128 may then determine whether the first image or video has been captured, e.g., by analyzing the images or videos captured by the camera 120, or by receiving an indication from the user, e.g., via the user interface 122, indicating that the first image or video has been captured.

Upon determining that the first image or video has been captured, the augmented reality repair application 128 may provide an augmented reality display overlay 208 for a second area or portion of the vehicle of which a second image or video must be captured, in a similar manner. Subsequently, upon determining that the second image or video has been captured, the augmented reality application 128 may provide an augmented reality display overlay 208 identifying an area or portion of the vehicle of which a third image or video that must be captured, and so on until all images or videos have been captured.

Figure 3B:
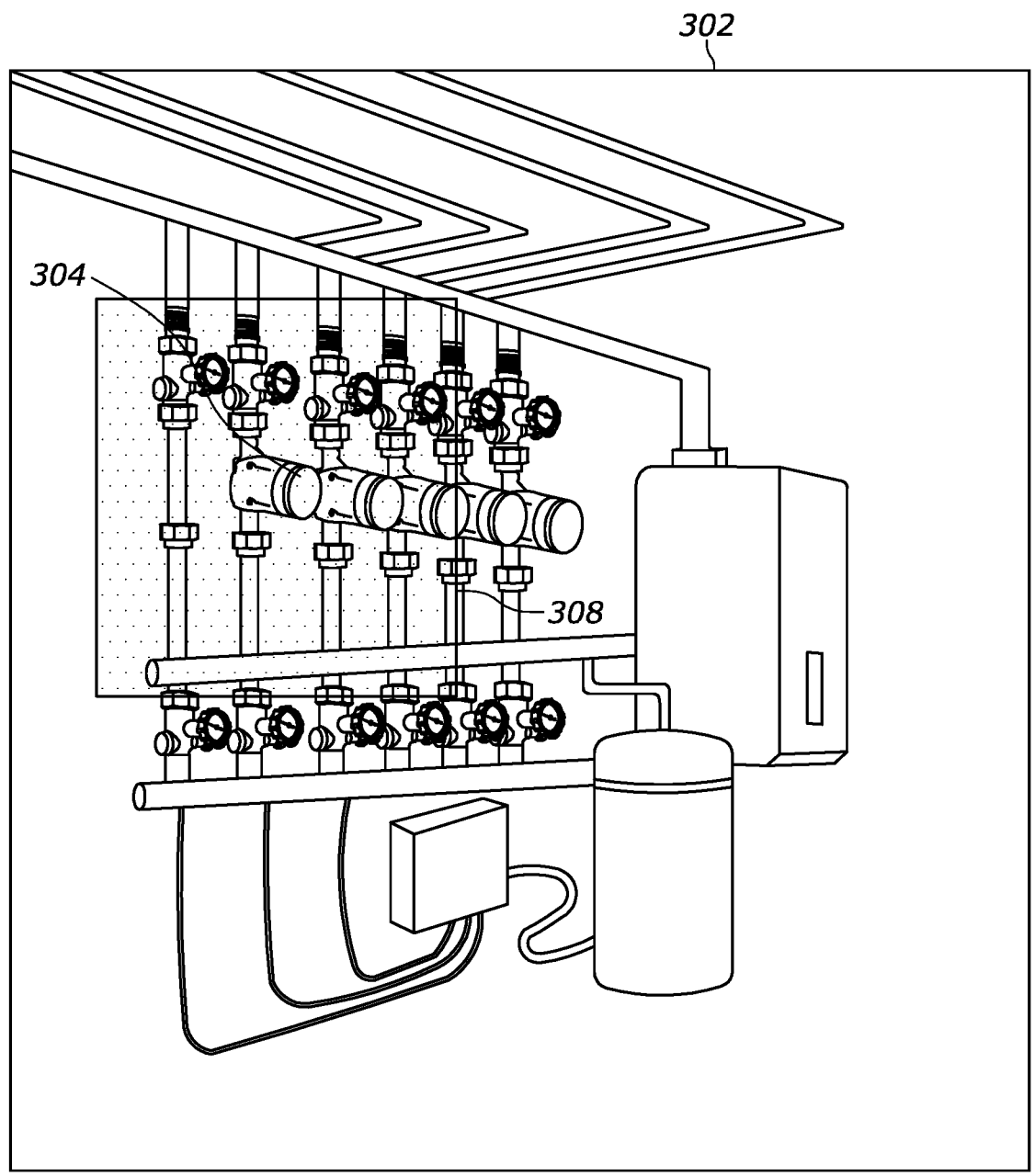
FIG. 3B depicts an exemplary augmented reality display identifying areas of home environment of which images may be captured in order to request a professional repair of a home appliance that is not functioning properly, and/or submit an insurance claim related to the home appliance that is not functioning properly, according to one embodiment.

An example of the augmented reality display overlay in the case of the home repair is shown at FIG. 3B. As shown at FIG. 3B, a view 302 of a portion of the vehicle (i.e., either images or videos captured by the camera 120 in real time, or a view through glasses or a window) may include at least one augmented reality display overlay 308 identifying or otherwise indicating a portion or area of the home environment of which an image or video must be captured. In examples in which multiple images or videos must be captured, the augmented reality repair application 128 may provide a first augmented reality display overlay 308 identifying a first portion or area of the home environment of which an image or video must be captured. The augmented reality repair application 128 may then determine whether the first image or video has been captured, e.g., by analyzing the images or videos captured by the camera 120, or by receiving an indication from the user, e.g., via the user interface 122, indicating that the first image or video has been captured.

Upon determining that the first image or video has been captured, the augmented reality repair application 128 may provide an augmented reality display overlay 308 for a second area or portion of the home environment of which a second image or video must be captured, in a similar manner. Subsequently, upon determining that the second image or video has been captured, the augmented reality application 128 may provide an augmented reality display overlay 308 identifying an area or portion of the home environment of which a third image or video that must be captured, and so on until all images or videos have been captured.

Executing the augmented reality repair application 128 may further include identifying one or more professionals who may be capable of performing the identified repair in a geographic region associated with the vehicle 110 or home environment 114, and sending the captured images, e.g., via the network 106, to a computing device associated with a professional who may be capable of performing the identified repair. Furthermore, executing the augmented reality repair application 128 may include sending the captured images, e.g., via the network 106, to an insurance provider who may provide coverage for the identified repair, and/or prepare a virtual insurance for the user's review, modification, approval, and/or submission.

For example, the augmented reality repair application or another application may present a virtual or electronic insurance claim (such as one prepared by one or more local or remote processors or servers) on the insured's or user's mobile or other device for the insured's or other user's review, modification, or approval. For instance, after the images or videos are captured by user's device, the image or video data may be transmitted to one or more local or remote processors and/or servers associated with an insurance provider or other entity for analysis. The local or remote processors or servers may generate a virtual insurance claim with pre-populated fields, and transmit the virtual insurance claim to the insured's or other user's mobile device, wearable, virtual or augmented reality headset or glasses, etc. for their review, modification, approval, and/or submission.

Moreover, in some examples, the computer-readable instructions stored on the memory 126 may include instructions for carrying out any of the steps of the methods 400 or 500 via an algorithm executing on the processors 124, which are described in greater detail below with respect to FIGS. 4 and 5.

In some embodiments the computing system 104 may comprise one or more servers, which may comprise multiple, redundant, or replicated servers as part of a server farm. In still further aspects, such server(s) may be implemented as cloud-based servers, such as a cloud-based computing platform. For example, such server(s) may be any one or more cloud-based platform(s) such as MICROSOFT AZURE, AMAZON AWS, or the like. Such server(s) may include one or more processor(s) 130 (e.g., CPUs) as well as one or more computer memories 132.

Memories 132 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. Memorie(s) 132 may store an operating system (OS) (e.g., Microsoft Windows, Linux, UNIX, etc.) capable of facilitating the functionalities, apps, methods, or other software as discussed herein. Memorie(s) 132 may also store a repair diagnostic application 134, a machine learning model training application 136, and/or a repair diagnostic machine learning model 138.

Additionally, or alternatively, the memorie(s) 132 may store historical vehicle repair data and/or historical home repair data. The historical vehicle repair data may also be stored in a historical vehicle repair database 140, which may be accessible or otherwise communicatively coupled to the computing system 104. Similarly, the historical home repair data may also be stored in a historical home repair database 142, which may be accessible or otherwise communicatively coupled to the computing system 104. In some embodiments, the historical vehicle repair data and/or historical home repair data, or other data from various sources may be stored on one or more blockchains or distributed ledgers.

Executing the repair diagnostic application 134 may include receiving the sensor data and/or operational data from the augmented reality repair application 128 of the mobile device 102, applying a trained repair diagnostic machine learning model 138 to the sensor data and/or operational data in order to identify vehicle components or home appliances in need of repair, and/or possible repairs for the identified vehicle components or home appliances, and sending the identified vehicle components or home appliances in need of repair, and/or possible repairs for the identified vehicle components or home appliances, to the augmented reality repair application 128 of the mobile device 102.

In some examples, the trained repair diagnostic machine learning model 138 may be executed on the computing system 104, while in other examples the repair diagnostic machine learning model 138 may be executed on another computing system, separate from the computing system 104. For instance, the computing system 104 may send the sensor data and/or operational data from the mobile device 102 to another computing system, where the trained repair diagnostic machine learning model 138 is applied to the sensor data and/or operational data, and the other computing system may send a prediction or identification of vehicle components or home appliances in need of repair, and/or possible repairs for the identified vehicle components or home appliances based upon applying the trained repair diagnostic machine learning model 138 to the sensor data and/or the operational data, to the computing system 104. Moreover, in some examples, the repair diagnostic machine learning model 138 may be trained by a machine learning model training application 136 executing on the computing system 104, while in other examples, the repair diagnostic machine learning model 138 may be trained by a machine learning model training application executing on another computing system, separate from the computing system 104.

Whether the repair diagnostic machine learning model 138 is trained on the computing system 104 or elsewhere, the repair diagnostic machine learning model 138 may be trained by the machine learning model training application 136 using training data corresponding to historical sensor data and/or historical operational data, and historical vehicle components or home appliances historically identified as being in need of repair, and/or historically successful repairs for the historically identified vehicle components or home appliances in need of repairs. The trained machine learning model may then be applied to new sensor data and/or new operational data in order to identify or predict, e.g., vehicle components or home appliances in need of repair, and/or possible repairs for the identified vehicle components or home appliances.

In various aspects, the repair diagnostic machine learning model 138 may comprise a machine learning program or algorithm that may be trained by and/or employ a neural network, which may be a deep learning neural network, or a combined learning module or program that learns in one or more features or feature datasets in particular area(s) of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques.

In some embodiments, the artificial intelligence and/or machine learning based algorithms used to train the repair diagnostic machine learning model 138 may comprise a library or package executed on the computing system 104 (or other computing devices not shown in FIG. 1). For example, such libraries may include the TENSORFLOW based library, the PYTORCH library, and/or the SCIKIT-LEARN Python library.

Machine learning may involve identifying and recognizing patterns in existing data (such as training a model based upon historical sensor data and/or operational data) in order to facilitate making predictions or identification for subsequent data (such as using the machine learning model on new sensor data and/or operational data in order to determine a prediction or identification of vehicle components or home appliances in need of repair, and/or possible repairs for the identified vehicle components or home appliances).

Machine learning model(s) may be created and trained based upon example data (e.g., "training data") inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, patterns, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based upon the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

In addition, memories 132 may also store additional machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For instance, in some examples, the computer-readable instructions stored on the memory 132 may include instructions for carrying out any of the steps of the methods 400 or 500 via an algorithm executing on the processors 130, which are described in greater detail below with respect to FIGS. 4 and 5. It should be appreciated that one or more other applications may be envisioned and that are executed by the processor(s) 130. It should be appreciated that given the state of advancements of mobile computing devices, all of the processes functions and steps described herein may be present together on a mobile computing device, such as the mobile computing device 102.

Figure 4:
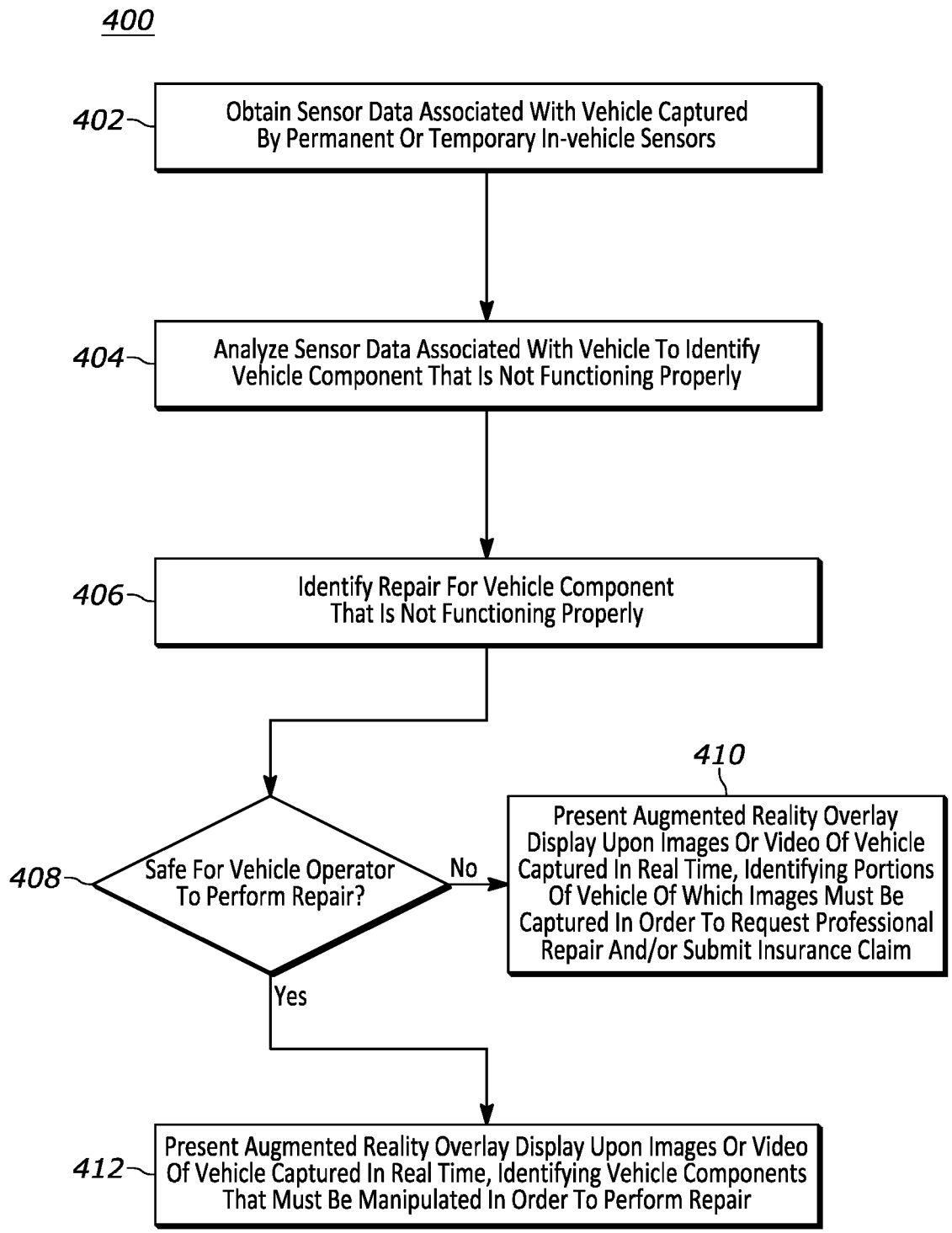
FIG. 4 depicts a flow diagram of an exemplary computer-implemented for providing augmented reality overlay displays related to vehicle repairs, according to one embodiment.

Exemplary Computer-Implemented Method for Providing Augmented Reality Overlay Displays Related to Vehicle Repairs FIG. 4 depicts a flow diagram of an exemplary computer-implemented method 400 for providing augmented reality overlay displays related to vehicle repairs, according to one embodiment. One or more steps of the method 400 may be implemented as a set of instructions stored on a computer-readable memory (e.g., memory 126, memory 132, etc.) and executable on one or more processors (e.g., processor 124, processor 130, etc.).

The method may begin when sensor data associated with a vehicle is obtained (block 402) or received. The sensor data may be captured by one or more permanent or temporary in-vehicle sensors. For instance, permanent in-vehicle sensors may be fixed, installed, or configured at various points inside and outside of the vehicle, while temporary in-vehicle sensors may include sensors associated with mobile computing devices that are temporarily located in the vehicle, e.g., while an operator is operating the vehicle.

Additionally, in some examples, operational data associated with the vehicle may be obtained or received. For instance, the operational data associated with the vehicle may include data generated by an onboard vehicle computing device, including indications of vehicle controls and/or operations performed by a vehicle operator, such as turning operations, steering operations, and/or braking operations, as well as air conditioning or heating operations, stereo or radio operations, turn signal operations, headlight (or other lighting) operations, operations involving adjustment of vehicle seating, operations involving adjustment of vehicle mirrors, etc.

The sensor data associated with the vehicle may be analyzed (block 404) in order to identify a vehicle component that is not functioning properly. In some examples, the vehicle operational data may be analyzed together with the sensor data in order to identify the vehicle component that is not functioning properly. Furthermore, in some examples the sensor data (and/or the vehicle operational data) may be analyzed by applying a trained machine learning model to the sensor data and/or the vehicle operational data in order to identify the vehicle component that is not functioning properly.

For instance, historical sensor data (and/or historical operational data) associated with respective historical vehicles over a historical period of time may be received or obtained, and historical vehicle components associated with the respective historical vehicles that were not functioning properly over the historical period of time may be received or obtained as well. The machine learning model may be trained using the historical sensor data (and/or historical operational data) associated with respective historical vehicles over the historical period of time, and the historical vehicle components associated with the respective historical vehicles that were not functioning properly over the historical period of time, such that the trained machine learning model is capable of identifying vehicle components of a vehicle that are not functioning properly based upon sensor data (and/or operational data) associated with the vehicle captured over a subsequent period of time.

At least one possible repair for the vehicle component that is not functioning properly may be identified (block 406). For instance, the repair may include physically manipulating various vehicle components, including the vehicle component that is not functioning properly and/or one or more other vehicle components, which may include switches, wires, tubing, pipes, or other mechanical parts associated with the vehicle. Moreover, the repair may include multiple steps, and/or multiple vehicle components that must be physically manipulated in order to complete the repair.

For instance, the method 400 may include identifying a first step or stage of the repair including a first vehicle component that must be physically manipulated, a second step or stage of the repair including a second vehicle component that must be physically manipulated (and/or a second way in which the first vehicle component must be physically manipulated), a third step or stage of the repair including a third vehicle component that must be physically manipulated (and/or another way in which the first or second vehicle component must be physically manipulated), etc.

In some examples, identifying the vehicle component that is not functioning properly, and/or identifying the possible repair, may include determining whether the vehicle component that is not functioning properly, and/or the possible repair, is covered by an existing vehicle insurance policy associated with the vehicle, and providing an indication to the user indicating whether the vehicle component that is not functioning properly, and/or the possible repair, is covered by an existing vehicle insurance policy associated with the vehicle.

A determination may be made as to whether it is safe for a vehicle operator to perform the at least one repair for the vehicle component that is not functioning properly (block 408). For instance, the determination may be made by analyzing each of the steps or stages of the repair to determine any potential health or safety risks associated with each step or stage of the repair. The potential health or safety risks may be assigned a health or safety risk score and the determination as to whether it is safe for the vehicle operator to perform the at least one repair may include comparing the health or safety risk score of the repair collectively, and/or of each of the individual steps or stages of the repair, to a threshold health or safety risk score.

Based upon determining that it is not safe (block 408, NO) for the vehicle operator to perform the at least one repair for the vehicle component that is not functioning properly, an augmented reality overlay display may be presented (block 410) upon images or video of the vehicle captured in real time, identifying portions of the vehicle of which the vehicle operator must capture images in order to one or more of: (i) request a professional repair of the vehicle component or (ii) prepare and/or submit an insurance claim related to the vehicle component that is not functioning properly. For instance, the augmented reality overlay display may initially identify a first portion of the vehicle of which an image or video must be captured. The images or video of the vehicle may continue to be captured in real time, and analyzed in order to determine whether the an image or video of the first portion of the vehicle has been successfully captured, at which point the augmented reality overlay display may be updated in order to identify a second portion of the vehicle of which an image or video must be captured, and so on for each portion of the vehicle of which an image or video must be captured.

In some examples, once images of all identified portions of the home environment have been successfully captured, a price estimate for a professional repair of the vehicle component may be generated and displayed. Furthermore, in some examples, once images of all identified portions of the vehicle have been successfully captured, a professional repair of the vehicle component may be automatically requested. For instance, one or more professionals in a geographic region associated with the vehicle that are capable of performing the repair may be identified, and a video call, voice call, text, email, or other request for repair may be sent to computing devices associated with the respective one or more professionals, including an indication of the vehicle component in need of repair and the captured images associated therewith. Additionally, in some examples, once images of all identified portions of the vehicle have been successfully captured, an insurance claim for the vehicle component may be automatically requested, including an indication of the vehicle component in need of repair and the captured images associated therewith.

Additionally or alternatively, the augmented reality repair application or another application may generate, receive, and/or present a virtual or electronic insurance claim (such as one prepared by one or more local or remote processors or servers) on the insured's or other user's mobile or other device (e.g., virtual reality or augmented reality headset or glasses) for the insured's or other user's review, modification, or approval. For instance, after the images or videos are captured by user's device, the image or video data may be transmitted to one or more local or remote processors and/or servers for analysis. The local or remote processors or servers may generate a virtual insurance claim with pre-populated fields, and transmit the virtual insurance claim to the insured's or other user's mobile device, wearable, virtual or augmented reality headset or glasses, etc. for their review, modification, approval, and/or submission.

Based upon determining that it is safe (block 408, YES) for the vehicle operator to perform the at least one repair for the vehicle component that is not functioning properly, an augmented reality overlay display may be presented (block 412) upon images or video of the vehicle captured in real time, identifying vehicle components that must be manipulated in order to perform the at least one repair. For instance, the augmented reality overlay display may initially identify a vehicle component that must be manipulated at a first stage or step of the repair. The images or video of the vehicle may continue to be captured in real time, and analyzed in order to determine whether the first step or stage of the repair has been completed, at which point the augmented reality overlay display may be updated in order to identify a vehicle component that must be manipulated at a second stage or step of the repair, and so on for each stage or step of the repair, until the repair is complete.

Figure 5:
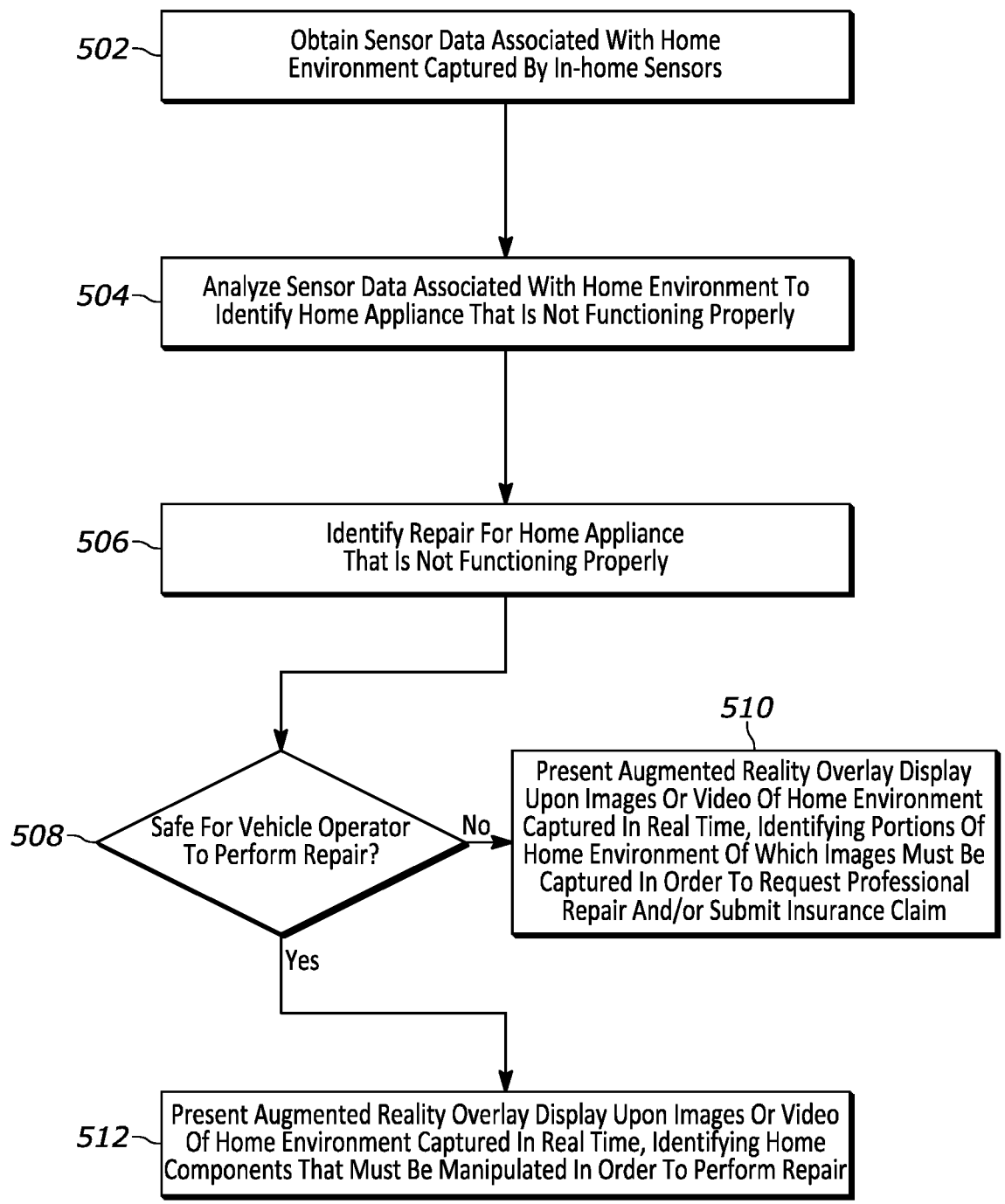
FIG. 5 depicts a flow diagram of an exemplary computer-implemented for providing augmented reality overlay displays related to vehicle repairs, according to one embodiment.

Exemplary Computer-Implemented Method for Providing Augmented Reality Overlay Displays Related to Home Repairs FIG. 5 depicts a flow diagram of an exemplary computer-implemented method 500 for providing augmented reality overlay displays related to home repairs, according to one embodiment. One or more steps of the method 500 may be implemented as a set of instructions stored on a computer-readable memory (e.g., memory 126, memory 132, etc.) and executable on one or more processors (e.g., processor 124, processor 130, etc.).

The method may begin when sensor data associated with a home environment is obtained (block 502) or received. The sensor data may be captured by one or more in-home sensors. For instance, in-home sensors may be fixed, installed, or configured at various points inside and outside of the home environment. Additionally, the sensor data may include data captured by mobile computing devices associated with residents of the home.

Additionally, in some examples, operational data associated with the home environment, or appliances within the home environment, may be obtained or received. For instance, the operational data associated with the home environment may include data generated by home appliances, including usage data indicating dates and/or times of use, types of use, durations of use, settings adjusted by users at various times, etc.

The sensor data associated with the home environment may be analyzed (block 504) in order to identify a home appliance that is not functioning properly. In some examples, the home operational data may be analyzed together with the sensor data in order to identify the home appliance that is not functioning properly. Furthermore, in some examples the sensor data (and/or the home operational data) may be analyzed by applying a trained machine learning model to the sensor data and/or the home operational data in order to identify the home appliance that is not functioning properly.

For instance, historical sensor data (and/or historical operational data) associated with respective historical home environments over a historical period of time may be received or obtained, and historical home appliances associated with the respective historical home environments that were not functioning properly over the historical period of time may be received or obtained as well. The machine learning model may be trained using the historical sensor data (and/or historical operational data) associated with respective historical home environments over the historical period of time, and the historical home appliances associated with the respective historical home environments that were not functioning properly over the historical period of time, such that the trained machine learning model is capable of identifying home appliances that are not functioning properly based upon sensor data (and/or operational data) associated with the home environment captured over a subsequent period of time.

At least one possible repair for the home appliance that is not functioning properly may be identified (block 506). For instance, the repair may include physically manipulating various components of the home environment or home appliance, including the home appliance that is not functioning properly and/or one or more other components, which may include switches, wires, tubing, pipes, or other mechanical parts associated with the home environment. Moreover, the repair may include multiple steps, and/or multiple components that must be physically manipulated in order to complete the repair.

For instance, the method 500 may include identifying a first step or stage of the repair including a first component that must be physically manipulated, a second step or stage of the repair including a second component that must be physically manipulated (and/or a second way in which the first component must be physically manipulated), a third step or stage of the repair including a third component that must be physically manipulated (and/or another way in which the first or second component must be physically manipulated), etc.

In some examples, identifying the home appliance that is not functioning properly, and/or identifying the possible repair, may include determining whether the home appliance that is not functioning properly, and/or the possible repair, is covered by an existing home insurance policy associated with the home, and providing an indication to the user indicating whether the home appliance that is not functioning properly, and/or the possible repair, is covered by an existing home insurance policy associated with the home.

A determination may be made as to whether it is safe for a resident of the home to perform the at least one repair for the home appliance that is not functioning properly (block 508). For instance, the determination may be made by analyzing each of the steps or stages of the repair to determine any potential health or safety risks associated with each step or stage of the repair. The potential health or safety risks may be assigned a health or safety risk score and the determination as to whether it is safe for the resident of the home to perform the at least one repair may include comparing the health or safety risk score of the repair collectively, and/or of each of the individual steps or stages of the repair, to a threshold health or safety risk score.

Based upon determining that it is not safe (block 508, NO) for the resident of the home to perform the at least one repair for the home appliance that is not functioning properly, an augmented reality overlay display may be presented (block 510) upon images or video of the home environment captured in real time, identifying portions of the home environment of which the resident of the home must capture images in order to one or more of: (i) request a professional repair of the home appliance, or (ii) prepare and/or submit an insurance claim related to the home appliance that is not functioning properly.

For instance, the augmented reality overlay display may initially identify a first portion of the home environment of which an image or video must be captured. The images or video of the home environment may continue to be captured in real time, and analyzed in order to determine whether the an image or video of the first portion of the home environment has been successfully captured, at which point the augmented reality overlay display may be updated in order to identify a second portion of the home environment of which an image or video must be captured, and so on for each portion of the home environment of which an image or video must be captured.

In some examples, once images of all identified portions of the home environment have been successfully captured, a price estimate for a professional repair of the home appliance may be generated and displayed. Furthermore, in some examples, a professional repair of the home appliance may be automatically requested. For instance, one or more professionals in a geographic region associated with the home that are capable of performing the repair may be identified, and a video call, voice call, text, email, or other request for repair may be sent to computing devices associated with the respective one or more professionals, including an indication of the home appliance in need of repair and the captured images associated therewith. Additionally, in some examples, once images of all identified portions of the home environment have been successfully captured, an insurance claim for the home appliance may be automatically requested, including an indication of the home appliance in need of repair and the captured images associated therewith.

Additionally or alternatively, the augmented reality repair application or another application may receive, generate, and/or present a virtual or electronic insurance claim (such as one prepared by one or more local or remote processors or servers) on the insured's or other user's device for the insured's or other user's review, modification, or approval. For instance, after the images or videos are captured by user's device, the image or video data may be transmitted to one or more local or remote processors and/or servers for analysis. The local or remote processors or servers may generate a virtual insurance claim with pre-populated fields, and transmit the virtual insurance claim to the insured's or other user's mobile device, wearable, virtual or augmented reality headset or glasses, etc. for their review, modification, approval, and/or submission.

Based upon determining that it is safe (block 508, YES) for the resident of the home to perform the at least one repair for the home appliance that is not functioning properly, an augmented reality overlay display may be presented (block 512) upon images or video of the home environment captured in real time, identifying components of the home appliance, or other components of the home, that must be manipulated in order to perform the at least one repair. For instance, the augmented reality overlay display may initially identify a component that must be manipulated at a first stage or step of the repair. The images or video of the home environment may continue to be captured in real time, and analyzed in order to determine whether the first step or stage of the repair has been completed, at which point the augmented reality overlay display may be updated in order to identify a component that must be manipulated at a second stage or step of the repair, and so on for each stage or step of the repair, until the repair is complete.

Figure 6:
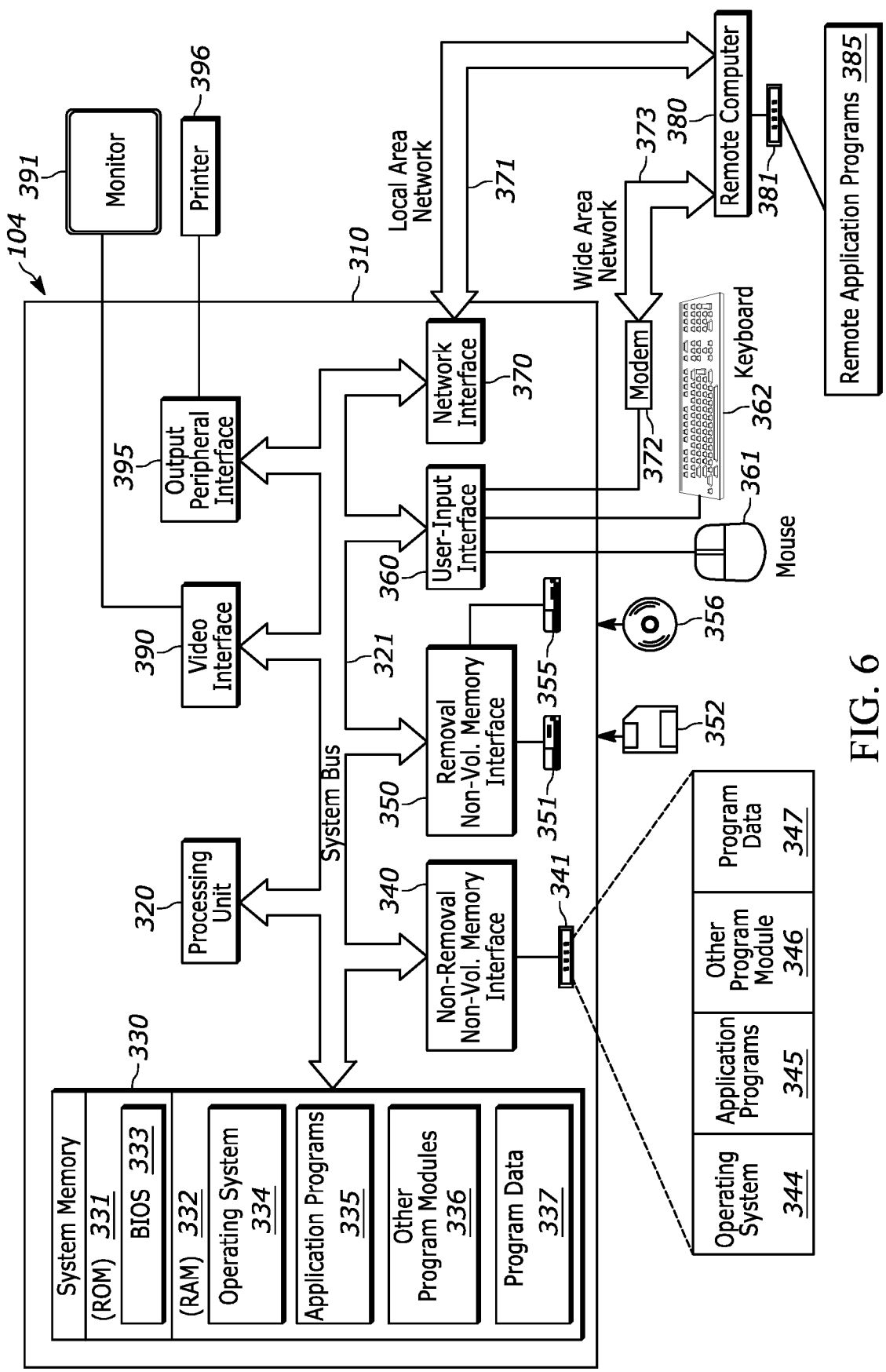
FIG. 6 depicts an exemplary computing system in which the techniques described herein may be implemented, according to one embodiment.

Exemplary Computing System for Providing Augmented Reality Overlay Displays Related to Repairs FIG. 6 depicts an exemplary computing system 104 in which the techniques described herein may be implemented, according to one embodiment. The computing system 104 of FIG. 6 may include a computing device in the form of a computer 310. Components of the computer 310 may include, but are not limited to, a processing unit 320 (e.g., corresponding to the processor 120 of FIG. 1), a system memory 330 (e.g., corresponding to the memory 122 of FIG. 1), and a system bus 321 that couples various system components including the system memory 330 to the processing unit 320. The system bus 321 may be any of several types of bus structures including a memory bus or memory controller, a peripheral bus, or a local bus, and may use any suitable bus architecture. By way of example, and not limitation, such architectures include the Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus (also known as Mezzanine bus).

Computer 310 may include a variety of computer-readable media. Computer-readable media may be any available media that can be accessed by computer 310 and may include both volatile and nonvolatile media, and both removable and non-removable media. By way of example, and not limitation, computer-readable media may comprise computer storage media and communication media.

Computer storage media may include volatile and nonvolatile, removable and non-removable media implemented in any method or technology for storage of information such as computer-readable instructions, data structures, program modules or other data. Computer storage media may include, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 310.

Communication media typically embodies computer-readable instructions, data structures, program modules or other data in a modulated data signal such as a carrier wave or other transport mechanism, and may include any information delivery media. The term "modulated data signal" means a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared and other wireless media. Combinations of any of the above are also included within the scope of computer-readable media.

The system memory 330 may include computer storage media in the form of volatile and/or nonvolatile memory such as read only memory (ROM) 331 and random access memory (RAM) 332. A basic input/output system 333 (BIOS), containing the basic routines that help to transfer information between elements within computer 310, such as during start-up, is typically stored in ROM 331. RAM 332 typically contains data and/or program modules that are immediately accessible to, and/or presently being operated on, by processing unit 320. By way of example, and not limitation, FIG. 6 illustrates operating system 334, application programs 335 (e.g., corresponding to the repair diagnostic application 134, machine learning model training application 136, repair diagnostic machine learning model 138, etc.), other program modules 336, and program data 337.

The computer 310 may also include other removable/non-removable, volatile/nonvolatile computer storage media. By way of example only, FIG. 6 illustrates a hard disk drive 341 that reads from or writes to non-removable, nonvolatile magnetic media, a magnetic disk drive 351 that reads from or writes to a removable, nonvolatile magnetic disk 352, and an optical disk drive 355 that reads from or writes to a removable, nonvolatile optical disk 356 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 341 may be connected to the system bus 321 through a non-removable memory interface such as interface 340, and magnetic disk drive 351 and optical disk drive 355 may be connected to the system bus 321 by a removable memory interface, such as interface 350.

The drives and their associated computer storage media discussed above and illustrated in FIG. 6 provide storage of computer-readable instructions, data structures, program modules and other data for the computer 310. In FIG. 6, for example, hard disk drive 341 is illustrated as storing operating system 344, application programs 345, other program modules 346, and program data 347.

Note that these components may either be the same as or different from operating system 334, application programs 335, other program modules 336, and program data 337. Operating system 344, application programs 345, other program modules 346, and program data 347 are given different numbers here to illustrate that, at a minimum, they are different copies. A user may enter commands and information into the computer 310 through input devices such as cursor control device 361 (e.g., a mouse, trackball, touch pad, etc.) and keyboard 362. A monitor 391 or other type of display device is also connected to the system bus 321 via an interface, such as a video interface 390. In addition to the monitor, computers may also include other peripheral output devices such as printer 396, which may be connected through an output peripheral interface 395.

The computer 310 may operate in a networked environment using logical connections to one or more remote computers, such as a remote computer 380. The remote computer 380 may be a mobile computing device, personal computer, a server, a router, a network PC, a peer device or other common network node, and may include many or all of the elements described above relative to the computer 310, although only a memory storage device 381 has been illustrated in FIG. 6. The logical connections depicted in FIG. 6 include a local area network (LAN) 371 and a wide area network (WAN) 373 (e.g., either or both of which may correspond to the network 108 of FIG. 1), but may also include other networks. Such networking environments are commonplace in hospitals, offices, enterprise-wide computer networks, intranets and the Internet.

When used in a LAN networking environment, the computer 310 is connected to the LAN 371 through a network interface or adapter 370. When used in a WAN networking environment, the computer 310 may include a modem 372 or other means for establishing communications over the WAN 373, such as the Internet. The modem 372, which may be internal or external, may be connected to the system bus 321 via the input interface 360, or other appropriate mechanism. The communications connections 370, 372, which allow the device to communicate with other devices, are an example of communication media, as discussed above. In a networked environment, program modules depicted relative to the computer 310, or portions thereof, may be stored in the remote memory storage device 381. By way of example, and not limitation, FIG. 6 illustrates remote application programs 385 as residing on memory device 381.

The techniques for providing augmented reality overlay displays related to repairs described above may be implemented in part or in their entirety within a computing system such as the computing system 104 illustrated in FIG. 6. In some such embodiments, the LAN 371 or the WAN 373 may be omitted. Application programs 335 and 345 may include a software application (e.g., a web-browser application) that is included in a user interface, for example.

Additional Considerations

The following additional considerations apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" or "some embodiments" means that a particular element, feature, structure, or characteristic described in connection with the embodiment is included in at least one embodiment. The appearances of the phrase "in one embodiment" or "in some embodiments" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" is employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for providing augmented reality overlay displays related to repairs. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-implemented method for providing augmented reality overlay displays related to vehicle repairs, comprising:
    obtaining, by one or more processors, sensor data associated with a vehicle captured by one or more permanent or temporary in-vehicle sensors;
    analyzing, by the one or more processors, the sensor data associated with the vehicle in order to identify a vehicle component that is not functioning properly;
    identifying, by the one or more processors, at least one possible repair for the vehicle component that is not functioning properly;
    determining, by the one or more processors, whether it is safe for a vehicle operator to perform the at least one repair for the vehicle component that is not functioning properly; and
    based upon determining that it is safe for the vehicle operator to perform the at least one repair for the vehicle component that is not functioning properly:
        presenting an augmented reality overlay display upon images or video of the vehicle captured in real time, wherein the augmented reality overlay display identifies vehicle components that must be manipulated in order to perform the at least one repair; or
    based upon determining that it is not safe for the vehicle operator to perform the at least one repair for the vehicle component that is not functioning properly:
        presenting an augmented reality overlay display upon images or video of the vehicle captured in real time, wherein the augmented reality overlay display identifies portions of the vehicle of which the vehicle operator must capture images in order to one or more of: (i) request a professional repair of the vehicle component or (ii) submit an insurance claim related to the vehicle component that is not functioning properly.

2. The computer-implemented method of claim 1, further comprising:
    receiving, by the one or more processors, operational data associated with the vehicle; and wherein analyzing the sensor data associated with the vehicle in order to identify the vehicle component that is not functioning properly includes analyzing both the sensor data associated with the vehicle and the operational data associated with the vehicle in order to identify the vehicle component that is not functioning properly.

3. The computer-implemented method of claim 1, wherein analyzing the sensor data associated with the vehicle in order to identify the vehicle component that is not functioning properly includes applying a trained machine learning model to the sensor data associated with the vehicle in order to identify the vehicle component that is not functioning properly.

4. The computer-implemented method of claim 3, further comprising:
    receiving, by the one or more processors, historical sensor data associated with respective historical vehicles over a historical period of time, and historical vehicle components associated with the respective historical vehicles that were not functioning properly over the historical period of time; and
    training, by the one or more processors, a machine learning model using the historical sensor data associated with respective historical vehicles over the historical period of time, and historical vehicle components associated with the respective historical vehicles that were not functioning properly over the historical period of time, such that the trained machine learning model is capable of identifying vehicle components of a vehicle that are not functioning properly based upon sensor data associated with the vehicle captured over a subsequent period of time.

5. The computer-implemented method of claim 1, wherein based upon determining that it is safe for the vehicle operator to perform the at least one repair for the vehicle component that is not functioning properly, the method further comprises:
    identifying, by the one or more processors, a first vehicle component that must be manipulated in order to complete a first stage of the at least one repair and a second vehicle component that must be manipulated in order to complete a second stage of the at least one repair, wherein the augmented reality overlay display initially identifies the first vehicle component that must be manipulated in order to complete the first stage of the at least one repair;
    analyzing, by the one or more processors, the images or video of the vehicle captured in real time to determine that the first vehicle component has been manipulated in order to complete the first stage of the at least one repair; and
    updating, by the one or more processors, the augmented reality overlay display in order to identify the second vehicle component that must be manipulated in order to complete the second stage of the at least one repair.

6. The computer-implemented method of claim 1, wherein based upon determining that it is not safe for the vehicle operator to perform the at least one repair for the vehicle component that is not functioning properly, the method further comprises:
    identifying, by the one or more processors, a first portion of the vehicle and a second portion of the vehicle of which images must be captured in order to one or more of: (i) request a professional repair of the vehicle component or (ii) submit an insurance claim related to the vehicle component that is not functioning properly, wherein the augmented reality overlay display initially identifies the first portion of the vehicle;
    analyzing, by the one or more processors, the images or video of the vehicle captured in real time to determine that an image of the first portion of the vehicle has been captured; and
    updating, by the one or more processors, the augmented reality overlay display in order to identify the second portion of the vehicle.

7. The computer-implemented method of claim 1, wherein based upon determining that it is not safe for the vehicle operator to perform the at least one repair for the vehicle component that is not functioning properly, the method further comprises:
    analyzing, by the one or more processors, the images or video of the vehicle captured in real time to determine that images of all identified portions of the vehicle have been captured; and based upon determining that images of all identified portions of the vehicle have been captured, one or more of: (i) automatically requesting a professional repair of the vehicle component or (ii) automatically submitting an insurance claim related to the vehicle component that is not functioning properly.

* * * * *